United States Patent
Suzuki et al.

(10) Patent No.: US 7,293,463 B2
(45) Date of Patent: Nov. 13, 2007

(54) ACOUSTOELECTRIC CONVERSION DEVICE

(75) Inventors: Kazuhiro Suzuki, Yokohama (JP); Hideyuki Funaki, Tokyo (JP); Yoshinori Iida, Tokyo (JP); Yujiro Naruse, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 112 days.

(21) Appl. No.: 11/116,273

(22) Filed: Apr. 28, 2005

(65) Prior Publication Data

US 2005/0241398 A1 Nov. 3, 2005

(30) Foreign Application Priority Data

Apr. 30, 2004 (JP) ............. 2004-136585

(51) Int. Cl.
*G01H 9/00* (2006.01)
*G01B 11/16* (2006.01)

(52) U.S. Cl. ............ 73/655; 73/649; 356/499

(58) Field of Classification Search ........ 73/655, 73/657, 647, 649; 359/285, 150, 151; 356/499; 381/186

See application file for complete search history.

(56) References Cited

U.S. PATENT DOCUMENTS 3,426,207 A * 2/1969 Fried et al. ............. 398/204
4,977,564 A * 12/1990 Ryu et al. ................. 372/32
5,235,607 A * 8/1993 Kojima et al. ......... 372/29.022
6,567,572 B2 * 5/2003 Degertekin et al. ........ 385/12
2003/0002129 A1 * 1/2003 Kobayashi et al. ......... 359/285
2005/0052724 A1 3/2005 Suzuki et al.

FOREIGN PATENT DOCUMENTS

| JP | 56-81802 | 7/1981 |
|---|---|---|
| JP | 7-249785 | 9/1995 |
| JP | 2000-292433 | * 10/2000 |
| JP | 2001-169395 | * 6/2001 |
| JP | 2001-231100 | 8/2001 |
| JP | 2001-292498 | 10/2001 |

* cited by examiner

*Primary Examiner*—Helen Kwok
(74) *Attorney, Agent, or Firm*—Oblon, Spivak, McClelland, Maier & Neustadt, P.C.

(57) ABSTRACT

In an acoustoelectric converter element, a light wave from a light source is introduced into a first optical waveguide of a vibration substrate, and diffracted by a diffraction grating disposed on the first optical waveguide. The diffracted light is directed to and detected by a photo detector. Here, the vibration substrate is so supported as to vibrate with respect to an acoustic wave. Therefore, the diffracted light detected by the photo detector is modulated by the acoustic wave, and a signal is output from the detector in accordance with the acoustic wave.

7 Claims, 14 Drawing Sheets

ACOUSTOELECTRIC CONVERSION DEVICE

CROSS-REFERENCE TO RELATED APPLICATIONS

This application is based upon and claims the benefit of priority from prior Japanese Patent Application No. 2004-136585, filed Apr. 30, 2004, the entire contents of which are incorporated herein by reference.

BACKGROUND OF THE INVENTION

1. Field of the Invention

The present invention relates to an acoustoelectric converter element, particularly to an acoustoelectric converter element which optically detects mechanical vibration due to an acoustic wave, thereby to convert the vibration into an electrical signal.

2. Description of the Related Art

As an acoustoelectric converter element which converts mechanical displacement based on an acoustic wave into an electrical signal, a microphone is known. A general microphone has a structure in which a diaphragm mechanically vibrated by the acoustic wave is incorporated, and the resonant frequency is uniquely determined by the mass and spring constant of the diaphragm. The frequency characteristic is said to be nominally flat, but sensitivity tends to drop apart from the resonant frequency inherent in the diaphragm. As a method of realizing a microphone having a broad dynamic range, a method in which a plurality of diaphragms having different diaphragm sizes and spring constants are arranged is reported in Jpn. Pat. Appln. KOKAI Publication Nos. 2001-292498 and 2001-231100.

On the other hand, there has been known a condenser microphone in which the vibration displacement of the diaphragm is generated due to a sound pressure and is detected as capacitance change. There is also known an optical microphone in which a light wave is irradiated on a diaphragm vibrating due to the sound pressure and a change of light intensity of the reflected light wave is detected as the vibration displacement. The condenser microphone and the optical microphone are disclosed in the Jpn. Pat. Appln. KOKAI Publication Nos. 2001-292498 and 2001-231100. In the optical microphone, superior characteristics are expected from viewpoints of directivity and resistance to noises as compared with the condenser microphone.

In a conventional optical microphone, a laser wave of gas laser, solid laser, or semiconductor laser diode is projected on the diaphragm and a change of light intensity of the reflected light wave is detected as the vibration displacement of the diaphragm. In the optical microphone which optically detects vibration amplitude of the diaphragm in this manner, an electrode or the like is not necessarily disposed on the back surface of the diaphragm. Therefore, the same space situation can be produced on front/back of the diaphragm, and therefore a sound pressure inclination microphone can be formed.

Moreover, there is a microphone array technique in which a plurality of condenser microphones are used, a delay sum is utilized, and accordingly single directivity is realized. A method is also used in which a pipe is additionally disposed in a part of an originally sealed vessel to supply outside air behind the diaphragm, the acoustic wave from the front is transmitted to the back surface of the diaphragm with delay to impart a "speed type" operation, and an operation of "single directivity" is performed as a whole. In the method proposed in the Jpn. Pat. Appln. KOKAI Publication Nos. 2001-292498 and 2001-231100, there is a disadvantage by a restriction of a mechanical structure or dimension. Since product groups increase in actual mounting, a drop of yield is feared.

Moreover, the conventional optical microphone disclosed in the Jpn. Pat. Appln. KOKAI Publication No. 2001-292498 is a reflective microphone. In the structure, high optical precision is required in an incidence optical system of incident light upon a diaphragm acting as the diaphragm and a reflection optical system which guides reflected light into a predetermined photo detector. Therefore, an optical fiber and a light guide have been used in order that the incident light and reflected light take arbitrary optical paths. Moreover, a lens device is disposed between a substrate on which a light receiving emitting device is mounted and the diaphragm, or another measure is taken in order to largely increase a movement width of the reflected light corresponding to the vibration displacement of the diaphragm. That is, in a conventional convergence grating system of the optical microphone, since the light wave reflected from the diaphragm spreads, great light intensity for detecting micro vibration displacement of the diaphragm by the photo detector to detect a difference of the light intensity is required, and therefore an assisting or correcting element for the optical path is required. Therefore, an optical device which realizes sophisticated positioning, and a new system are required in addition to the light emitting and receiving device and the diaphragm, and high-precision optical alignment is required. Therefore, there is possibility that drop of yield of a product is caused. Accordingly, a cost of the system rises. In a case where the optical fiber or the light guide is used, there is a problem that use range and application are largely limited. As understood from the structure, the light reflecting microphone has a problem that miniaturization is difficult.

The optical microphone capable of realizing sharp directivity with a simple structure is very useful, light source, diaphragm, photo detecting device need to be disposed in strictly appropriate positions, and difficulty at an assembling time is involved. Since the above-described three devices are individually introduced into the conventional optical microphone, a large space is wasted for the alignment of the devices. There is a great demand for arrangement in a limited small space in a microphone system. It can be easily speculated that it is difficult to adapt the existing optical microphone to the system, because the microphone has to take a large two or three-dimensional space.

BRIEF SUMMARY OF THE INVENTION

According to an aspect of the present invention, there is provided an acoustoelectric converter element for converting an acoustic wave to an electrical signal utilizing a light wave, comprising:

a substrate having a first optical waveguide into which the light wave is introduced;

a diaphragm comprising a diffraction grating which is so supported by the substrate as to vibrate with respect to the acoustic wave and which diffracts the light wave propagating through the first optical waveguide; and a photo detector which detects the diffracted light from the diffraction grating.

Moreover, according to another aspect of the present invention, there is provided an acoustoelectric converter element for converting an acoustic wave to an electrical signal utilizing a light wave, comprising:

a substrate including optical waveguide;

a diaphragm comprising a diffraction grating which is so supported on a substrate as to vibrate with respect to an acoustic wave and which is irradiated with the light wave and diffracts the light wave toward the optical waveguide; and a photo detector configured to detect the diffracted light guided in the optical waveguide.

DETAILED DESCRIPTION OF THE INVENTION

An acoustoelectric converter element according to embodiments will be described hereinafter with reference to the drawings.

Figure 1:
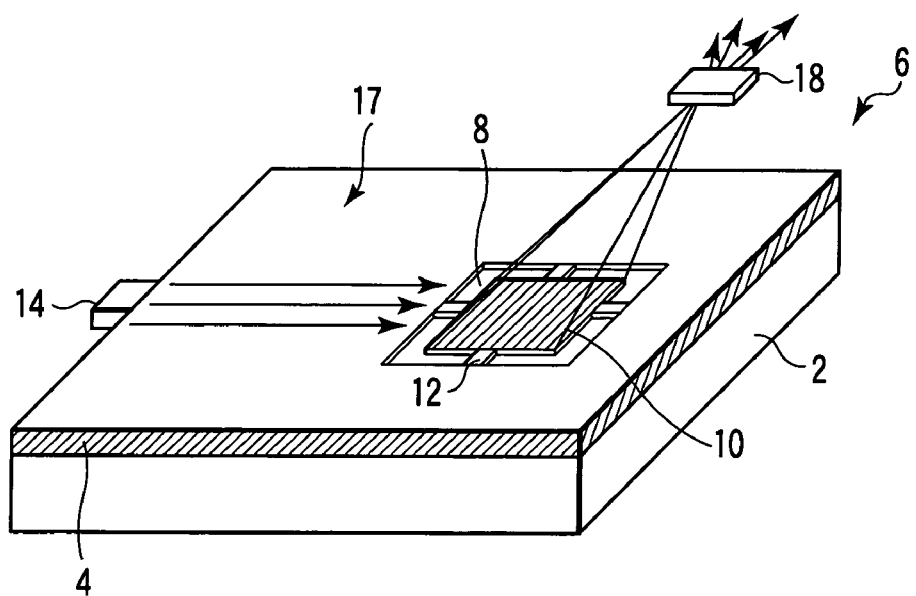
FIG. 1 is a perspective view schematically showing an acoustoelectric converter element according to one embodiment of the present invention.

FIG. 1 is a perspective view schematically showing an acoustoelectric converter element according to one embodiment of the present invention. In an acoustoelectric converter element shown in FIG. 1, a waveguide layer 4 guiding a light wave and having a refractive index nf is formed on a substrate 2 having a refractive index ns. The device has a stacked structure 6 of the substrate 2 and the waveguide layer 4 on the substrate 2. A cavity or a hollow portion 8 is formed to form a frame member 17 in the stacked structure 6, a focusing grating coupler (FGC) 10 acting as a diaphragm or a vibration plate is disposed in the hollow portion 8, and the FGC 10 is supported in the frame member 17 by a waveguide portion 12 having a substantially same structure as that of the waveguide layer 4. That is, the FGC 10 acting as the diaphragm is coupled to the frame member 17 via the waveguide portion 12 having a spring function in such a manner as to slightly vibrate with respect to an acoustic wave directed from the outside. Here, the FGC 10 hung in the frame member 17 has a mechanical vibration characteristic in such a manner that sensitivity is indicated at an audio frequency (e.g., 20 Hz to 20 kHz).

Moreover, a laser diode (LD) 14 is disposed at a side of the stacked structure 6, and irradiates the FGC 10 with a light wave 16 via the waveguide layer 4 and the support portion 12. In this FGC 10, a photo detector (PD) 18 is disposed outside the stacked structure 6, to which a specific direction component of a diffracted light is directed and which detects the light wave of the specific direction component. The diffraction light component forms a diffraction pattern on the photo detector (PD) 18, is detected by the photo detector (PD) 18, light intensity on the photo detector (PD) 18 is varied, and an output signal is output from the photo detector (PD) 18 in accordance with vibration of the FGC 10. That is, the light wave emitted from the LD 14 propagates through the waveguide 4 between an air layer having a refractive index nc and the substrate 2 having the refractive index ns, and enters the spring waveguide portion 12 connected to the FGC 10. The light wave entered in the FGC 10 via the waveguide portion 12 is emerged to a free space from the FGC 10, and detected in the photo detector (PD) 18.

In the acoustoelectric converter element shown in FIG. 1, the acoustic wave from the outside causes vibration in the FGC 10 suspended in the frame member 17, and a light wave guided into the FGC 10 is modulated by the vibration of the FGC 10. Modulation of the light wave is detected as a change of distribution of the diffraction pattern on the photo detector (PD) 18, and light intensity change of the diffraction pattern is output as the change of an electronic signal from the photo detector (PD) 18. The output signal is amplified, and output as a microphone output from a necessary circuit. According to the structure shown in FIG. 1, the acoustic vibration is output as an electrical signal, and the structure is capable of functioning as a microphone.

In the waveguide layer structure shown in FIG. 1, if the substrate 2 is made of a transparent refractive member having the refractive index ns, a transparent layer having the refractive index nf larger than the refractive index ns of the substrate 2 is disposed as the waveguide 4 on the substrate 2. Instead of the optically transparent waveguide 4, a structure may be simply formed into a stacked structure forming the waveguide 4 which comprises a core layer having the refractive index nf, and a cladding layer having the refractive index ns. That is, the core layer having the refractive index nf larger than the refractive index ns of the substrate 2 is disposed as the waveguide 4, and the cladding layer having the refractive index ns smaller than the refractive index nf of the transparent core layer may be disposed on this transparent core layer. If the substrate 2 is not a refractive member, a first cladding layer having the refractive index ns is disposed on the substrate 2, a transparent core layer having the refractive index nf larger than that of the first cladding layer is disposed as the waveguide 4, and a second cladding layer having the refractive index ns smaller than that of the transparent core layer may be disposed on the transparent core layer. In any case, the waveguide 4 is not limited to the above described structures as long as the light wave having a predetermined intensity can be efficiently transmitted to the FGC 10.

The FGC 10 is referred to as a convergence grating coupler or a focus grating coupler. In the FGC, a diffraction grating is formed on the surface of a waveguide layer structure, and has a lens function of focusing the light wave in a specific direction. The diffraction grating may be a one-dimensional diffraction grating in which linear grooves and ridges are arranged in parallel with one another at a predetermined pitch, or a two-dimensional diffraction grating in which prism-shaped convex and concave portions are arranged at a predetermined pitch in a matrix form. The diffraction grating formed in the FGC 10 is not limited to a case where the grating is disposed as a periodic shape change such as a concave/convex portion. A region where diffraction is periodically varied may be disposed in a flat layer, and a change of the refractive index corresponding to the concave/convex portion may be optically imparted to form the grating.

In the FGC 10, coupling between a waveguide mode and a radiation mode occurs, if a grating period satisfies a certain condition. This grating is used as an input/output coupler for exciting a guided light wave, or extracting the guided light wave to the outside. Therefore, as described above, the grating of this type is so called as the focus grating coupler or the convergence grating coupler. In the following description, simply the FGC (abbreviation of the focusing grating coupler) will be referred to.

A basic concept of the FGC 10 which focuses the light wave in the free space will be described hereinafter. Additionally, the following description is disclosed in "Optical Integrated Circuit authored by Hiroshi Nishihara, Masamitsu Haruna, and Toshiaki Kusuhara, and published by Ohm-sha (1985)".

Figure 2:
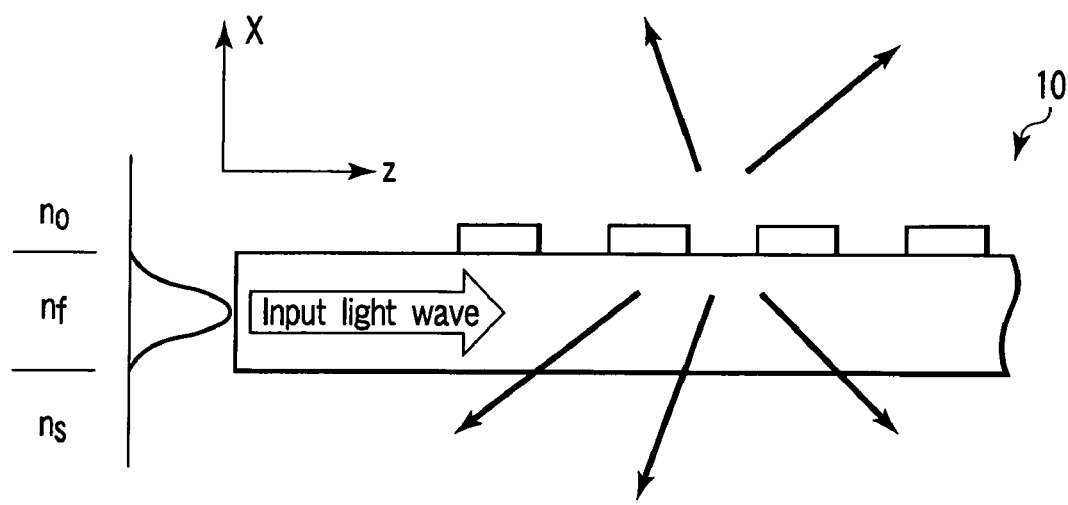
FIG. 2 is an explanatory view schematically showing a coupling state of waveguide mode and radiation mode at a FGC in which waveguide light rays are guided as shown in FIG. 1.
Figure 3:
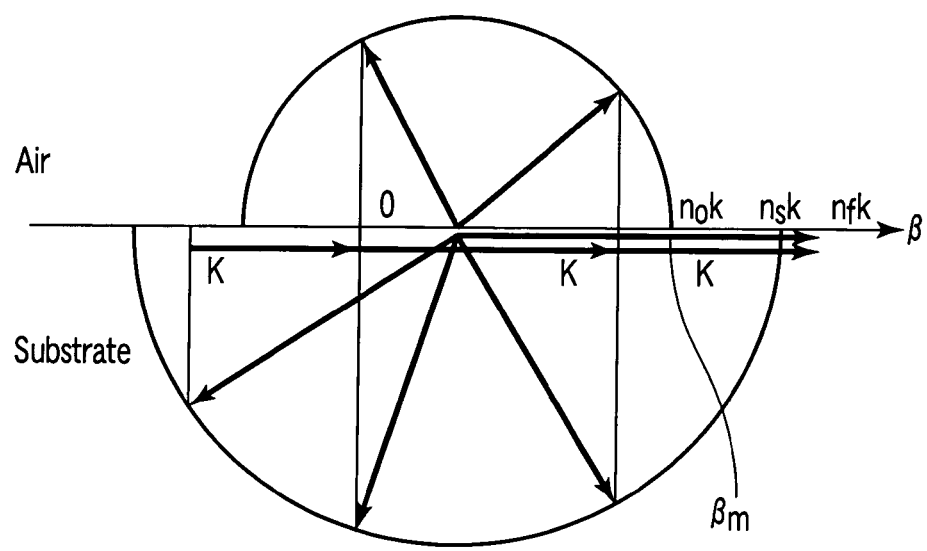
FIG. 3 is a diagram showing a propagation vector of diffracted light rays shown in FIG. 2.

An example of coupling of the waveguide mode and the radiation mode is shown in FIGS. 2 and 3, in a transmission of the waveguide light wave which is incident upon the FGC 10 and is guided in the FGC. Here, FIG. 2 schematically shows that the light wave propagates, and is diffracted, and FIG. 3 shows a vector component of a diffracted light wave. The incident light wave spreads along a waveguide plane (yz plane) of a two-dimensional waveguide, and the light wave is represented by the following equation (1):

$$\Delta\epsilon(x, y) = \Sigma\Delta\epsilon_q(x)\exp(-jqKz)(K=2\pi/\Lambda, \Delta\epsilon_q=\Delta\epsilon^*_q) \quad (1),$$

where $\Delta\epsilon_q$ denotes a change of distribution of specific permittivity $\epsilon_q$ based on the grating disposed on a two-dimensional waveguide optical path.

In a grating, if a waveguide light having a propagation constant $\beta_0=Nk$ (>0) propagates in the z-direction in this two-dimensional waveguide optical path structure, a space higher harmonic wave having a z-direction propagation constant $\beta_q$ represented by the following equation (2) is generated accompanying the light wave:

$$\beta_q=\beta_0+qK(q=0, \pm1, \pm2, \ldots) \quad (2),$$

where N denotes an equivalent refractive index of a propagating mode in a waveguide layer, K is a vector vertical to a grating plane and referred to as a grating vector, and $\Lambda$ denotes a basic period of the grating.

Assuming that refractive indexes of the substrate, waveguide layer, and upper clad layer are $n_s$, $n_f$, $n_c$, and an order q exists satisfying $|\beta_q|=n_ck$ or $|\beta_q|=n_sk$ in the space higher harmonic wave, radiation is performed as determined by equation (3) on an air or substrate side of the higher harmonic wave:

$$n_ck \sin\theta_q^{(c)}=n_sk \sin\theta_q^{(s)}=\beta_q=nk+qK \quad (3),$$

where $\theta_q^{(c)}$ and $\theta_q^{(s)}$ denote propagation angles of the radiated higher harmonic wave.

At this time, the wave which propagates in the grating coupler leaks to the outside of the waveguide by radiation. The grating is long in the z-direction, and thin in the x-direction. Therefore, the only equation (3) of phase matching in the z-direction may be satisfied between coupled surges, and a propagation vector diagram is shown in FIG. 3. A radiated beam generated by this coupling is determined by real number values of the propagation angles $\theta_q^{(c)}$, $\theta_q^{(s)}$ which establish the equation (3).

Considering from $n_c<n_s<N<n_f$ in the equation (3), the radiation is limited to an order of $q\leq-$. It is seen that a certain order only includes radiation on the substrate side only and radiation on both the substrate and air sides. FIG. 3 shows an example in which three or more beams are generated with a plurality of orders, and is referred to as multi-beam coupling. The number of emitted beams in radiation of a basic order (q=-1) is determined by K/k, N, equation (3). When the waveguide light enters the focus grating coupler, the above-described output coupling occurs. If this grating pattern is modulated, various wave front conversions can be executed simultaneously with the waveguide mode and the radiation mode coupling. As disclosed above, the focusing grating coupler (FGC) for focusing the waveguide light on the point of the free space can be realized. With utilizing this concept of the FGC, the optical microphone having a structure described above with reference to FIG. 1 can be realized.

Figure 4:
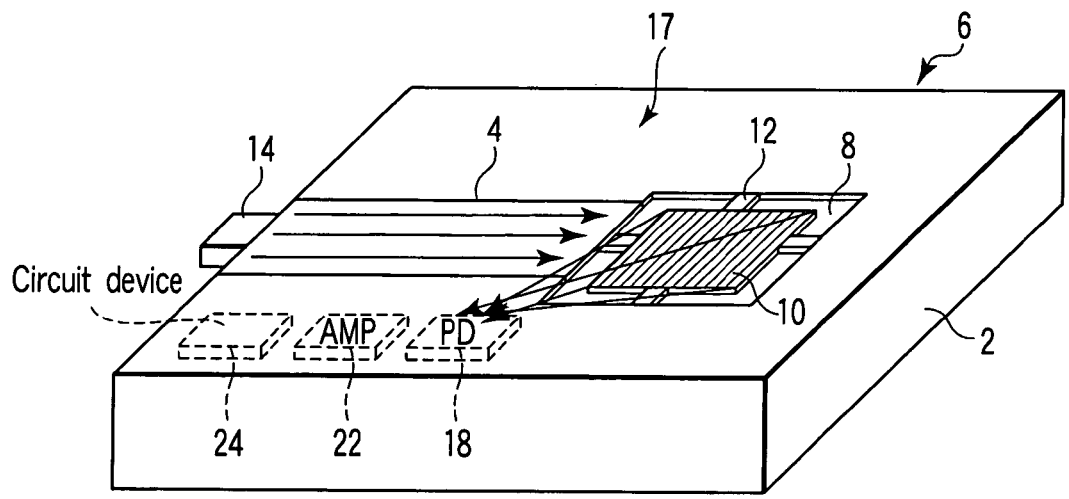
FIG. 4 is a perspective view schematically showing an acoustoelectric converter element according to another embodiment of the present invention.

As apparent from the above-described basic principle of the FGC 10, a light output from the FGC 10 can be directed not only on an air layer side but also on a substrate 2 side. Therefore, as shown in FIG. 4, the photo detector 18 can be formed on the same substrate 2. If an amplifier 22 and a processing circuit 24 are integrated in addition to the photo detector 18, an optical microphone can be realized, which hardly requires any space in a three-dimensional space direction.

The light wave emitted from the LD 14 propagates through the waveguide layer 4, and enters the waveguide portion 12 coupled to the FGC 10 in the acoustoelectric converter element shown in FIG. 4. The light wave entered in the FGC 10 through the waveguide portion 12 is radiated into the substrate 2, and a part of the wave is focused on the photo detector (PD) 18 via the waveguide portion 12 and the transparent substrate 2. Therefore, if the acoustic wave from the outside causes the vibration of the FGC 10, the light wave guided into the FGC 10 is modulated by the vibration of the FGC 10. On the photo detector (PD) 18, the modulation of the light wave is detected as the change of the distribution of the diffraction pattern, and the light intensity change of the diffraction pattern is output as the change of the electronic signal from the photo detector (PD) 18. The output signal is amplified by the amplifier 22, and output as a microphone output from the circuit 24.

Figure 5:
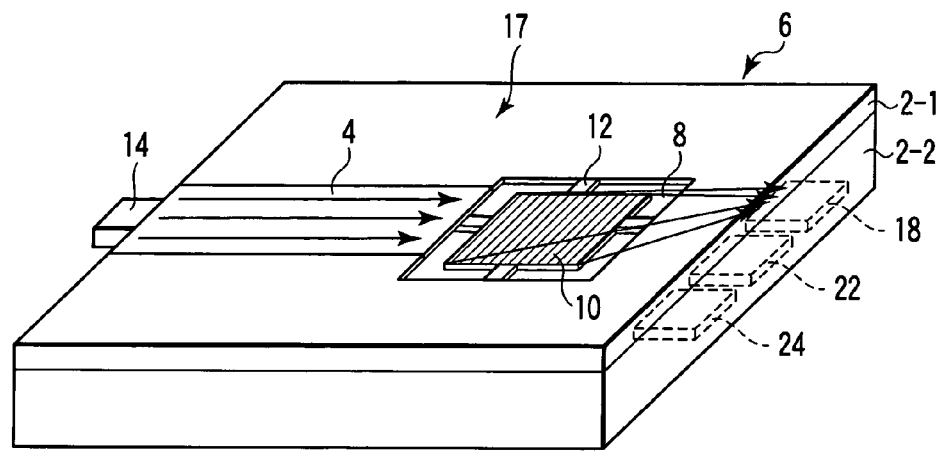
FIG. 5 is a perspective view schematically showing an acoustoelectric converter element according to still another embodiment of the present invention.

FIG. 5 shows that a first semiconductor substrate 2-1 on which an FGC 10 is formed and a second semiconductor substrate 2-2 on which a photo detector 18 is formed are separately manufactured, and laminated onto each other. An acoustoelectric converter element having the structure shown in FIG. 5 operates in the same manner as in that shown in FIG. 4, and an acoustic wave is detected.

Here, the photo detector 18, an amplification circuit 22, and a signal processing circuit 24 may be formed on the first semiconductor substrate 2-1 on which the FGC 10 is formed, or on another substrate 2-2. Here, a waveguide layer 4 may be formed with a single refractive index, or a certain refractive index distribution is imparted in such a manner as to focus the light wave on a waveguide portion 12, and a lens function may be provided.

Figure 6:
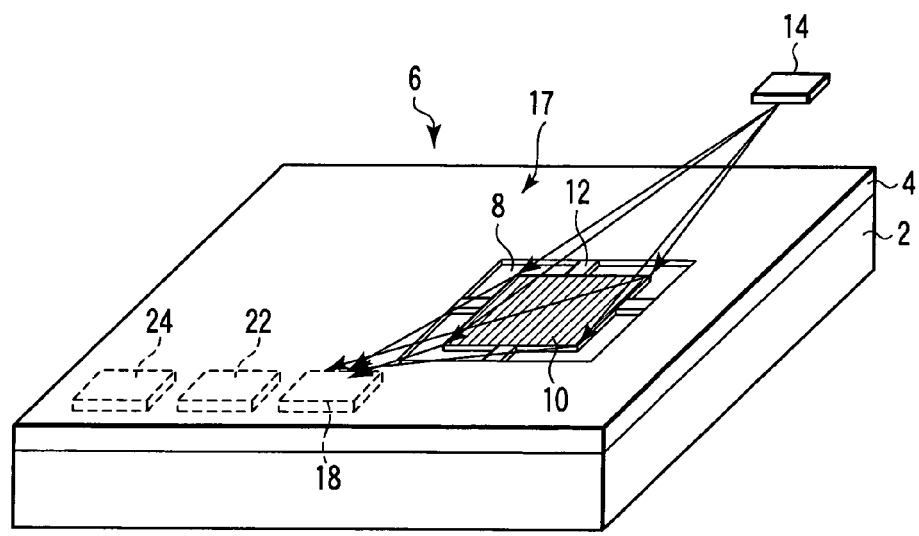
FIG. 6 is a perspective view schematically showing an acoustoelectric converter element according to still another embodiment of the present invention.
Figure 7:
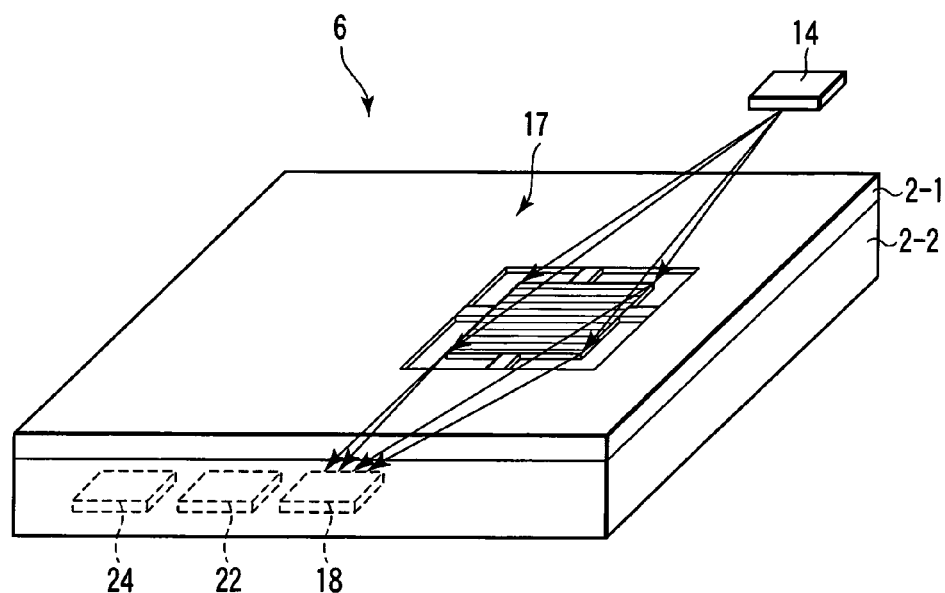
FIG. 7 is a perspective view schematically showing an acoustoelectric converter element according to still another embodiment of the present invention.

As described above, the FGC 10 has a characteristic that the radiated light wave from the FGC 10 can be emitted to a free space. The radiated light wave from the free space can be guided into the substrates 1, 2-1, 2-2 by the FGC 10 because of reversibility of a light wave path. Therefore, as shown in FIGS. 6 and 7, a laser diode 14 is provided as a light source at the outside of the transparent substrates 2, 2-1, 2-2, and diffracted light rays from the FGC 10 may be directed to a photo detector 18 through the waveguide portion 12 and the transparent substrates 2, 2-1, 2-2. In an arrangement shown in FIGS. 6 and 7, the light wave is not directed to the FGC 10 via the waveguide layer 4. The light wave from the laser diode 14 is directly transferred to the FGC 10 via a space, diffracted in the FGC 10, and guided into the substrates 2, 2-1, 2-2. Here, if the substrates 2, 2-1, 2-2 are provided with appropriate refractive indexes with respect to a surrounding atmosphere, for example, air, a part of the light wave diffracted by the FGC 10 is confined in the coupler, and can be guided into the photo detector 18.

It is to be noted that FIG. 6 shows a structure in which the FGC 10, photo detector 18, amplification circuit 22, and signal processing circuit 24 are formed on a single substrate 2, and FIG. 7 shows a structure in which the FGC 10 is formed on a first substrate 2-1, and the photo detector 18, amplification circuit 22, and signal processing circuit 24 are formed on a second substrate 2-2.

A light wave propagating to the FGC 10 through the waveguide layer 4 as described with reference to FIG. 3 is directed in a three-dimensional direction including a travel direction of the light wave by the diffraction grating of the FGC 10. Therefore, in an optical system shown in FIGS. 4 to 7, in principle, even if the photo detector 18 is disposed in any direction in which the light wave diffracted by the FGC 10 is directed, the diffracted light rays can be detected. That is, even in a case where the photo detector 18 is disposed in a space or substrate in a direction opposite to the travel direction of the light wave traveling to the diffraction grating, the photo detector 18 is capable of detecting the light wave diffracted by the diffraction grating. In a diffraction grating of a parallel type in which ridges and grooves are arranged in parallel with one another, even if the light wave enters the diffraction grating from a direction oblique or parallel with respect to the parallel grating as shown in FIG. 6, the similarly diffracted light is similarly directed in a three-dimensional direction, and can be detected by the photo detector 18. However, the light wave preferably enters the parallel diffraction grating from a direction substantially vertical to the direction of the grating as shown in FIG. 1, 5, or 7. As shown in FIG. 5 or 7, the photo detector 18 is preferably disposed in a travel direction of the light wave. If the light wave is substantially vertically entered in a grating arrangement direction of the parallel type diffraction grating, the incident light wave is more largely diffracted as compared with a case where the light wave enters the parallel diffraction grating from an arrangement direction. The diffracted light rays diffracted by the diffraction grating is directed from the diffraction grating with a larger diffraction light component in a travel direction of the incident light wave, and a travel direction space including the travel direction. In the optical system shown in FIG. 6, since the light wave enters the parallel grating from an oblique or parallel direction, a component diffracted by the diffraction grating is smaller than that of another optical system. Therefore, light intensity of the diffracted light rays detected by the photo detector 18 is sometimes reduced. It is preferable to dispose a light source 14 as shown in FIG. 7 as compared with the optical system shown in FIG. 6. Here, the photo detector 18 is preferably disposed in the travel direction of the incident light wave, and the travel direction space including the travel direction. However, if the photo detector 18 is disposed in the travel direction, most of the light wave may not be diffracted and directly enters in the photo detector 18. Therefore, the photo detector 18 is more preferably disposed in a peripheral space of the travel direction, excluding the travel direction of the incident light wave.

One embodiment of a method of manufacturing the optical integrated microphone shown in FIG. 1 will be described with reference to FIGS. 8A to 8E.

Figure 8A:
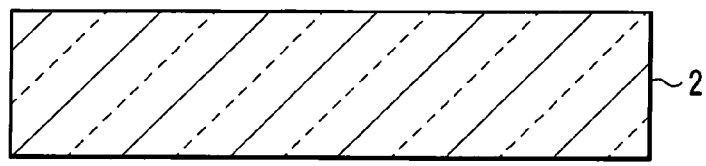
FIGS. 8A to 8E are sectional views schematically showing steps of a method of preparing an optical integrated microphone shown in FIG. 1.
Figure 8B:
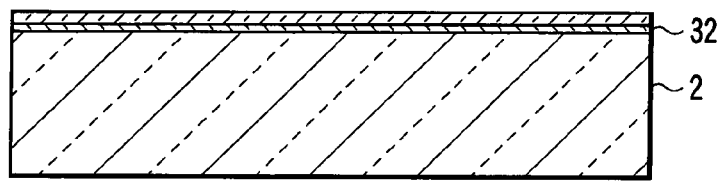

As shown in FIG. 8A, a silicon substrate is prepared as a semiconductor substrate 2. In the silicon substrate used as the semiconductor substrate 2 in which an optical waveguide is formed, a refractive index is comparatively high ($n_s$=3.42, $\lambda$=1 µm), and therefore a buffer layer 32 is preferably formed before forming the waveguide layer 4 as shown in FIG. 8B. Examples of a material suitable for the buffer layer 32 include SiO2 ($n_b$=about 1.5). The buffer layer 32 is formed on the semiconductor substrate 2, for example, the silicon substrate by a sputtering process or a CVD process.

Next, as shown in FIG. 8B, a material constituting a waveguide layer 4 is formed on the buffer layer 32. A material whose refractive index is slightly higher than that of the buffer layer 32 is used in the waveguide layer 4. As a material of the waveguide layer 4, for example, $Si_3N_4$ is assumed as preferable in the above-described structure, because a refractive index is $n_f$=about 2. A layer of $Si_3N_4$ is similarly formed by sputtering or CVD. As the material of the waveguide layer 4, organic materials may be used such as PMMA, polymer, and photo resist in addition to $Si_3N_4$. Here, it is necessary to form the buffer layer 32 and waveguide layer 4 into desired shapes.

Figure 8C:
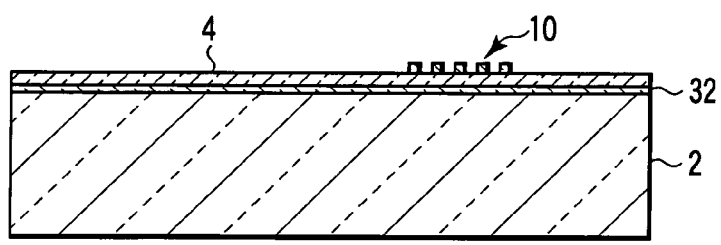

Thereafter, as shown in FIG. 8C, a grating portion of the FGC 10 is formed in a region on the waveguide layer 4. A conventional photolithography technique is applied to the forming of the grating portion of the FGC 10. That is, a plurality of layers for the diffraction grating are formed on the region on the waveguide layer 4 using a material similar to that of the waveguide layer 4, and a mask. Thereafter, the region on the grating layer is coated with the photo resist, a diffraction grating pattern is transferred and exposed, and the photo resist is formed into a mask for the grating. A grating layer is etched utilizing the mask for the grating to form the diffraction grating. Thereafter, the photo resist is removed, and a substrate structure in which the diffraction grating is formed on the waveguide layer 4 is prepared.

Figure 8D:
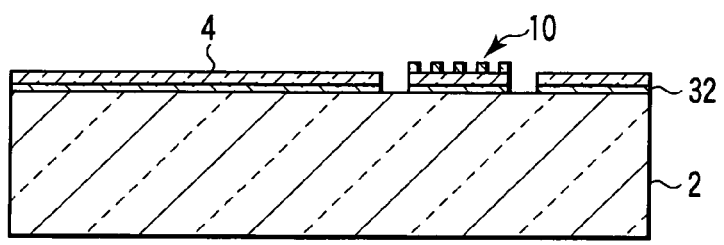

Next, as shown in FIG. 8D, the region of the FGC 10 is formed into a diaphragm shape using a photolithography technique and etching. Here, the waveguide portion 12 which is a spring for supporting the diaphragm is formed into a part of the waveguide of the waveguide layer 4 formed on the substrate 2. That is, the waveguide layer 4 having the substrate structure shown in FIG. 8C is similarly coated with the photo resist, a diaphragm pattern is transferred and exposed, and a mask having the patterns of the diaphragm and waveguide portion is prepared. The waveguide layer 4 is selectively etched using the mask to form the diaphragm and the waveguide portion 12 for supporting the plate. Thereafter, the photo resist is removed, and the substrate structure is prepared in which the FGC 10 and the waveguide portion 12 are independently formed on the substrate 2.

Figure 8E:
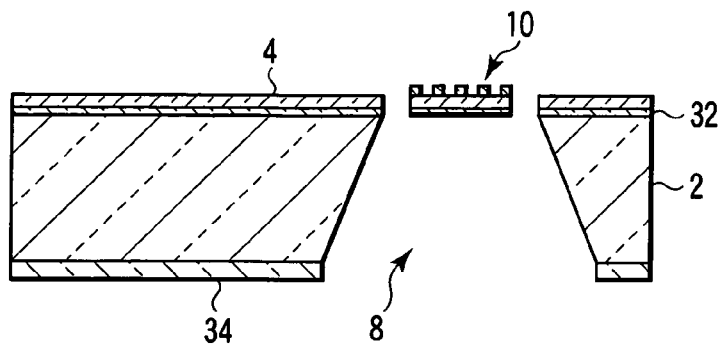

Finally, the diaphragm on which the FGC 10 is formed is separated from the substrate 2 using wet etching or the like as shown in FIG. 8E. As shown in FIG. 8E, a mask 34 is formed on the back surface of the substrate 2, and a hollow portion 8 is formed in the back surface of the FGC 10 by anisotropic etching. Here, it has been described that a hollowing process is anisotropically performed by the wet etching, but the present invention is not limited to this example. The process may be isotropically performed by a dry process. As to the device in which the optical waveguide 4 is prepared by the above-described steps, an LD chip 14 is coupled to the optical waveguide 4 to complete an optical integrated microphone.

Figure 9A:
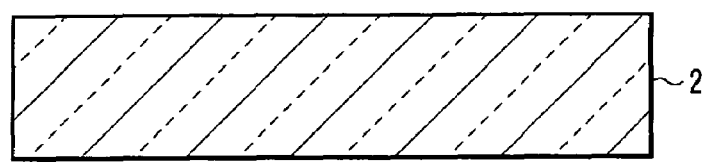
FIGS. 9A to 9F are sectional views schematically showing steps in a method of manufacturing an optical integrated microphone shown in FIG. 4.
Figure 9B:
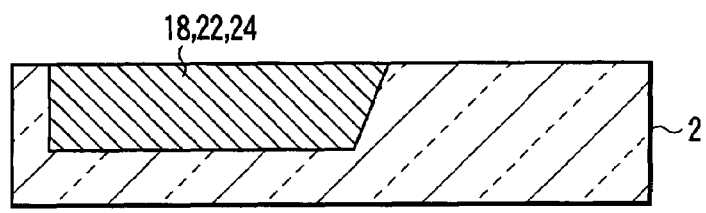
Figure 9C:
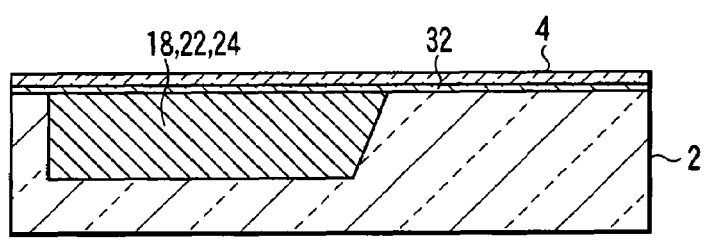
Figure 9D:
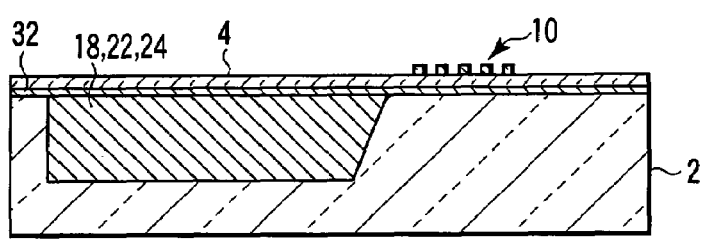
Figure 9E:
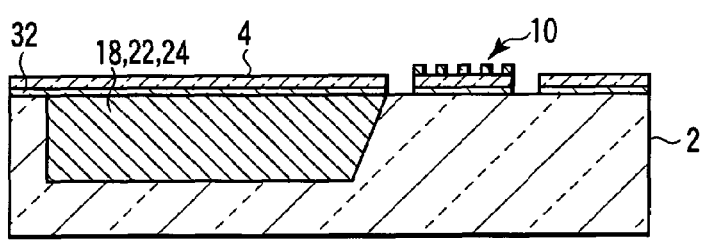
Figure 9F:
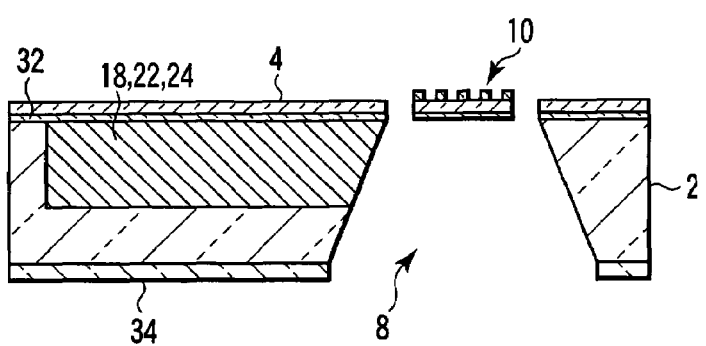

In the steps shown in FIGS. 8A and 8B, the optical waveguide is formed without forming any device on the semiconductor substrate 2. However, as shown in FIGS. 9A to 9C, an amplification circuit 22 and a processing circuit 24 may be formed in a semiconductor substrate 2 before forming an optical waveguide 4. That is, as shown in FIG. 9A, the semiconductor substrate 2 is prepared. Next, as shown in FIG. 9B, the photo detector 18, amplification circuit 22, and processing circuit 24 are formed in the semiconductor substrate 2. Thereafter, as shown in FIG. 9C, a buffer layer 32 and waveguide layer 4 may be formed. In FIGS. 9A to 9C, FIGS. 9C, 9D, 9E, and 9F correspond to FIGS. 8B, 8C, 8D, and 8E. Therefore, for the description of the steps of FIGS. 9C, 9D, 9E, and 9F, refer to the description of the steps of FIGS. 8B, 8C, 8D, and 8E.

Figure 10A:
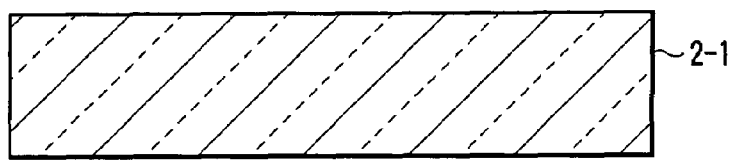
FIGS. 10A to 10F are sectional views schematically showing steps in a method of manufacturing an optical integrated microphone shown in FIG. 5.
Figure 10B:
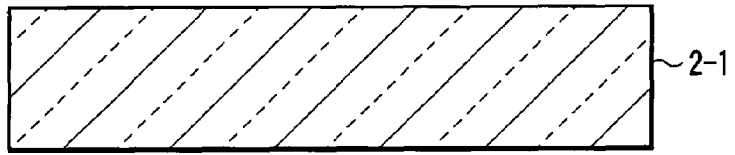
Figure 10C:
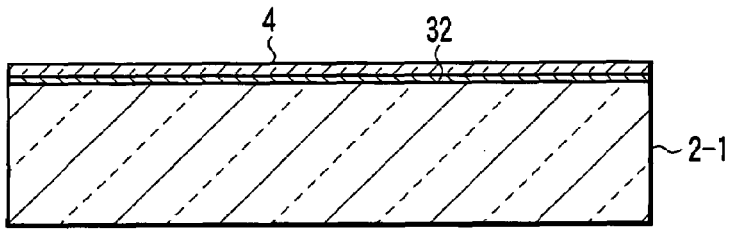
Figure 10D:
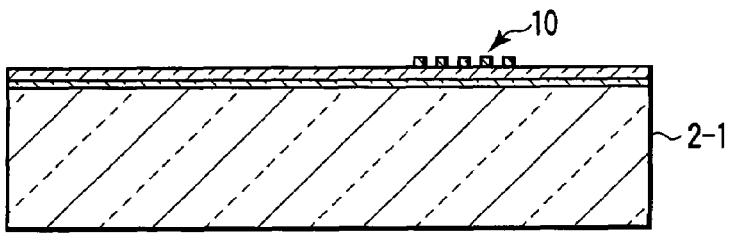
Figure 10E:
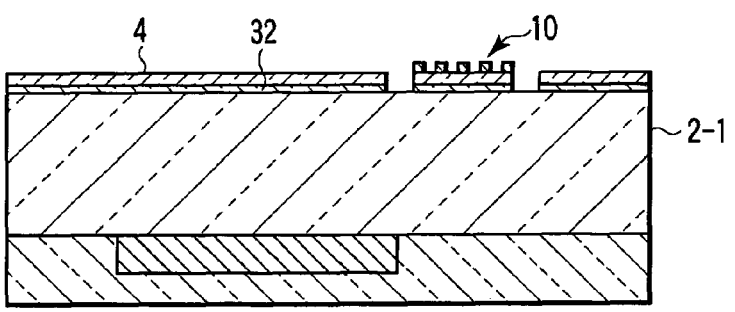
Figure 10F:
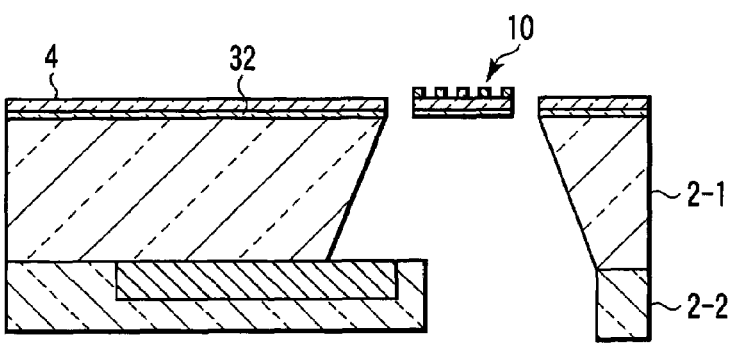

FIGS. 10A to 10F show steps of preparing a second substrate 2-2 on which a semiconductor device 18, amplification circuit 22, and processing circuit 24 are formed, and laminating the substrate onto a semiconductor substrate 2 on which an FGC 10 is formed to manufacture an optical integrated microphone. Since steps of FIGS. 10A to 10D are similar to those of FIGS. 8A to 8D, the description is omitted. As shown in FIG. 10E, a first substrate 2-1 is prepared on which a region of the FGC 10 is formed into a diaphragm shape using a photolithography technique and etching, a separately prepared second substrate 2-2 is closely attached to the back surface of the first substrate 2-1, and both the substrates are bonded to each other. Thereafter, as shown in FIG. 10F, a mask (not shown) is disposed on the back surface of the second substrate 2-2. Predetermined regions of the first and second substrates 2-1, 2-2 are etched by anisotropic etching using this mask to form a hollow portion 8 in the back surface of the waveguide layer 4.

Figure 11:
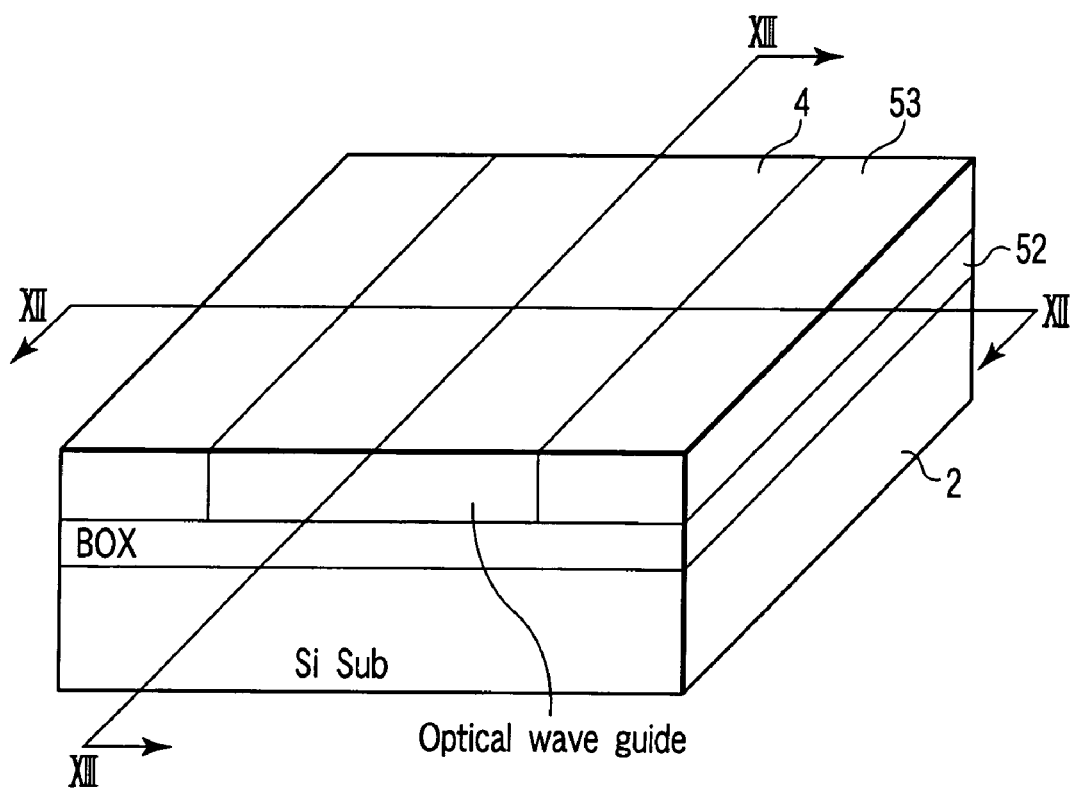
FIG. 11 is a perspective sectional view schematically showing a structure in which an optical waveguide is incorporated into an SOI substrate to realize the optical integrated microphone shown in FIG. 1.

As described above, when a highly refractive material is used like silicon in the substrate 2, there is a demand for the forming of a buffer layer 32. However, if an SOI substrate is used, a filling oxide film layer may be used as the buffer layer 32. FIG. 11 shows an example of a structure of an optical waveguide formed using the SOI substrate. As shown in FIG. 11, in the SOI substrate structure, a filling insulating film (SOI oxide film) 52, and a single crystal Si layer (SOI layer) 53 are successively stacked on a support substrate 2 formed of single crystal Si. Even if an SOI substrate structure 60 is used, the above-described preparation process can be adapted.

A step of forming an FGC 10 in the SOI substrate structure will be described with reference to FIGS. 12A to 12E and FIGS. 13A to 13E. Here, FIGS. 12A to 12E show a section along line XII-XII shown in FIG. 11, and FIGS. 13A to 13E show a section along line B-B' shown in FIG. 11.

Figure 12A:
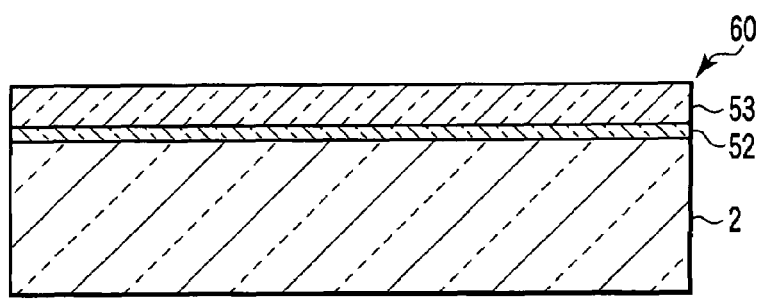
FIGS. 12A to 12E are sectional views along a line XII-XII in the SOI substrate structure shown in FIG. 11, schematically showing the steps of the method of manufacturing the optical integrated microphone shown in FIG. 1.
Figure 12B:
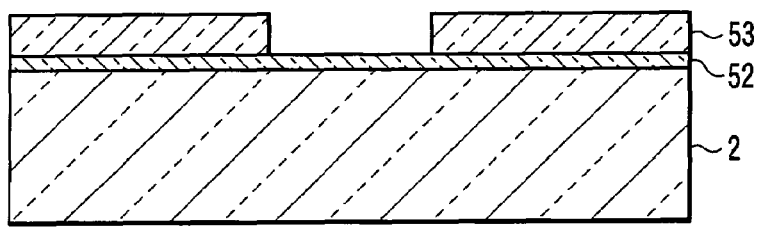
Figure 13A:
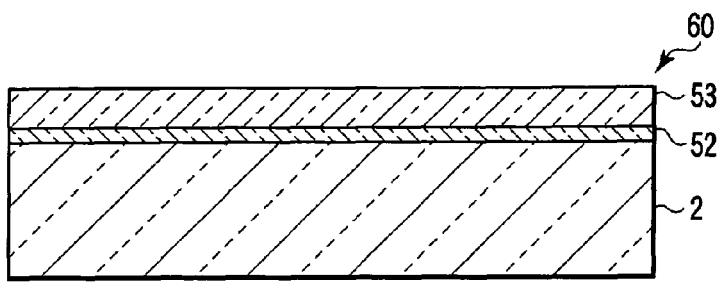
FIGS. 13A to 13E are sectional views along a line XIII-XIII in the SOI substrate structure shown in FIG. 11, schematically showing the steps of the method of manufacturing the optical integrated microphone shown in FIG. 1.
Figure 13B:
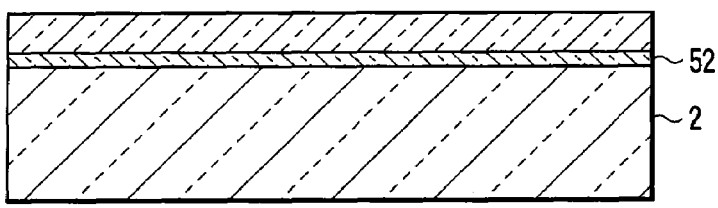

As shown in FIGS. 12A and 13A, the SOI substrate structure 60 is prepared in which the filling insulating film (SOI oxide film) 52 and the single crystal Si layer (SOI layer) 53 are successively stacked on the Si substrate 2. Next, as shown in FIGS. 12B and 13B, the single crystal Si layer 53 is selectively etched and removed by a technique, for example, a reactive ion etching (RIE) process, and the single crystal Si layer 53 corresponding to a region of a waveguide layer 4 is removed in a band shape.

Figure 12C:
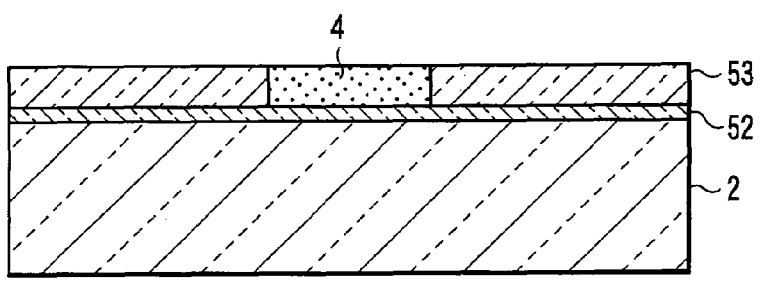

Next, the waveguide layer 4 is formed into the band-shaped region as shown in FIG. 12C. A material having a refractive index slightly higher than that of the filling insulating film 52 which is a buffer layer is used in the waveguide layer 4. Examples of the waveguide layer 4 include $Si_3N_4$. A layer of $Si_3N_4$ is similarly formed by sputtering or CVD. As the material of the waveguide layer 4, in addition to $Si_3N_4$, organic materials may be used such as PMMA, polymer, and photo resist. Here, it is necessary to form the waveguide layer 4 into a desired shape.

Figure 13C:
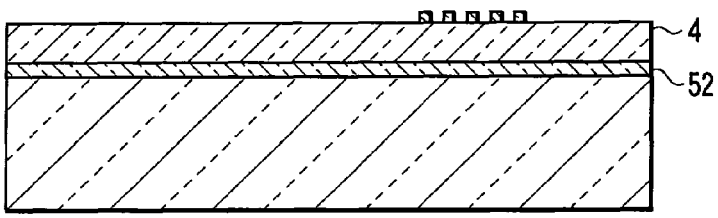

Furthermore, as shown in FIG. 13C, a grating portion of the FGC 10 is formed in a region on the waveguide layer 4. A plurality of layers for diffraction grating is formed in the region on the waveguide layer 4 using a material similar to that of the waveguide layer 4, and a mask. Thereafter, the region on this grating layer is coated with the photo resist, a diffraction grating pattern is transferred and exposed, and the photo resist is formed into a mask for the grating. The grating layer is selectively etched using the mask for the grating to form the diffraction grating, and the photo resist is removed.

Figure 12D:
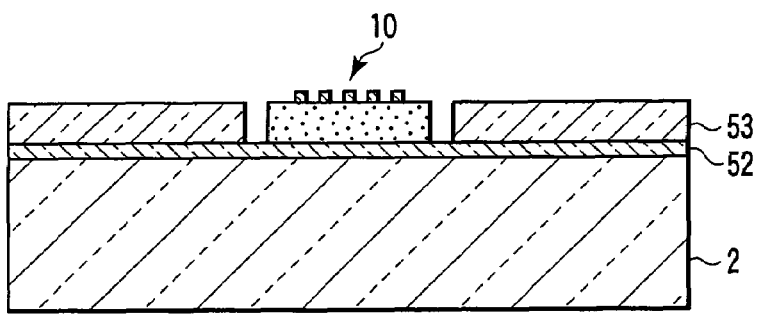
Figure 13D:
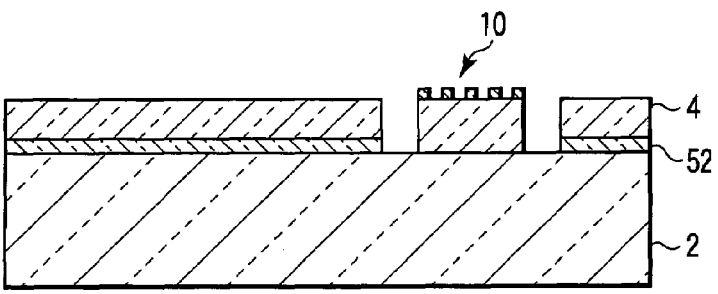

Thereafter, as shown in FIGS. 12D and 13D, the region on the waveguide layer 4 is formed into the FGC 10 which acts as a diaphragm. A conventional photolithography technique is similarly applied in forming the FGC 10. That is, the photo resist is applied to a region on the waveguide layer 4 of the substrate structure shown in FIG. 13C, a diaphragm pattern is transferred/exposed, and a mask having patterns of the diaphragm and waveguide portion is prepared. The waveguide layer 4 is selectively etched using this mask to form the diaphragm and a waveguide portion 12 for supporting the plate. Thereafter, the photo resist is removed, and a substrate structure is prepared in which the FGC 10 and the waveguide portion 12 are independently formed on the substrate 2. Here, the waveguide portion 12 which is a spring for supporting the diaphragm is formed as a part of the waveguide of the waveguide layer 4 formed on the substrate 2.

Figure 12E:
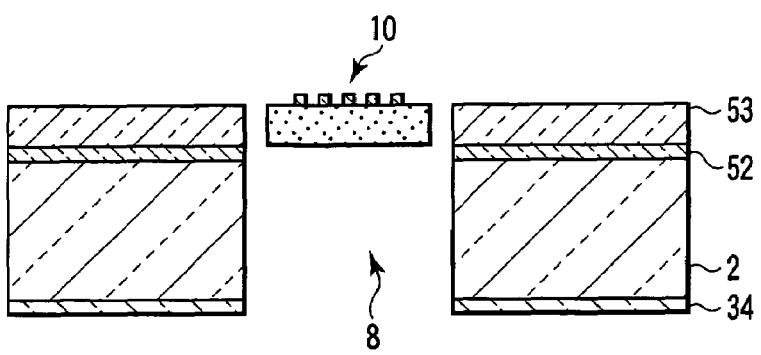
Figure 13E:
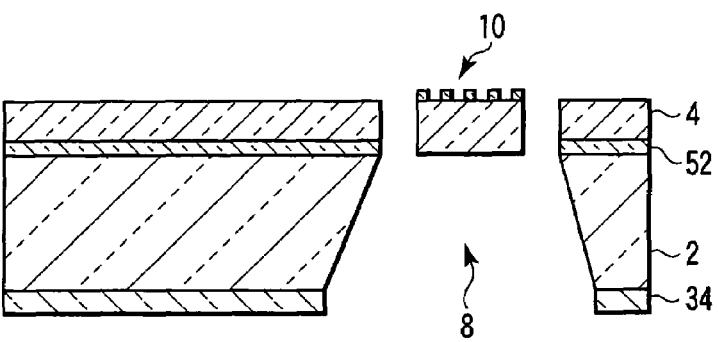

Finally, as shown in FIGS. 12E and 13E, the diaphragm on which the FGC 10 is formed is separated from the substrate 2 using wet etching or the like. As shown in FIGS. 12E and 13E, a mask 34 is formed on the back surface of the substrate 2, and a hollow portion 8 is formed in the back surface of the FGC 10 by anisotropic etching. Here, it has been described that this hollowing process is anisotropically performed by the wet etching. The present invention is not especially limited to this example. The process may be isotropically performed by a dry process. As to a device in which the optical waveguide 4 is prepared by the above-described steps, an LD chip 14 is coupled with the optical waveguide 4 to complete an optical integrated microphone.

According to the above-described steps, the device can be formed in the SOI substrate structure 60, and the steps are therefore useful for a structure which requires integration of a high-pressure resistant device.

FIGS. 14A and 14B, and FIGS. 15A and 15B show steps of forming a waveguide 4 and an FGC 10 on an SOI substrate structure. A method of manufacturing an acousto-electric converter element will be described with reference to FIGS. 14A and 14B, and FIGS. 15A and 15B. Here, FIGS. 14A to 14E correspond to a section along a line XIV-XIV shown in FIG. 11, and FIGS. 15A to 15E correspond to a section along a line XV-XV shown in FIG. 11. Additionally, It is to be noted that structures shown in FIGS. 14A and 14B, and FIGS. 15A and 15B are different from the structure shown in FIG. 11.

Figure 14A:
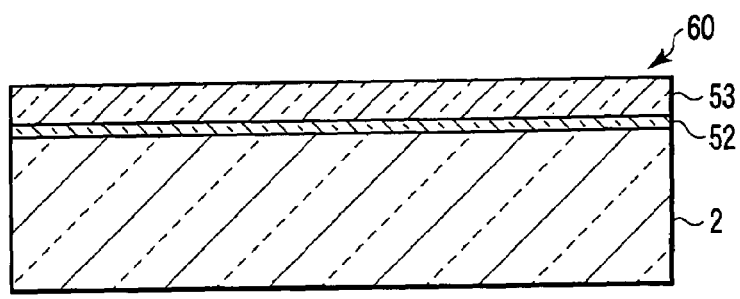
FIGS. 14A to 14E are sectional views along a line XII-XII in the SOI substrate structure shown in FIG. 11, schematically showing the steps of another method of manufacturing the optical integrated microphone shown in FIG. 1.
Figure 15A:
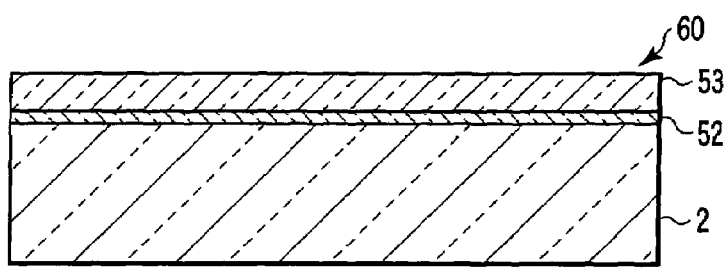
FIGS. 15A to 15E are sectional views along a line XIII-XIII in the SOI substrate structure shown in FIG. 11, schematically showing the steps of another method of manufacturing the optical integrated microphone shown in FIG. 1.

First, as shown in FIGS. 14A and 15A, a substrate structure 60 is prepared in which a filling insulating film (SOI oxide film) 52, and a single crystal Si layer (SOI layer) 53 are successively stacked on a Si substrate 2. Next, a mask for forming a waveguide layer 4 on the surface of the substrate structure is disposed, and the waveguide layer 4 is formed by a material whose refractive index is slightly higher than that of the single crystal Si layer (SOI layer) 53. Examples of a material of the waveguide layer 4 include $Si_3N_4$ as described above. A layer of $Si_3N_4$ is similarly formed by sputtering or CVD. As the material of the waveguide layer 4, organic materials may be used such as PMMA, polymer, and photo resist in addition to $Si_3N_4$.

Figure 14B:
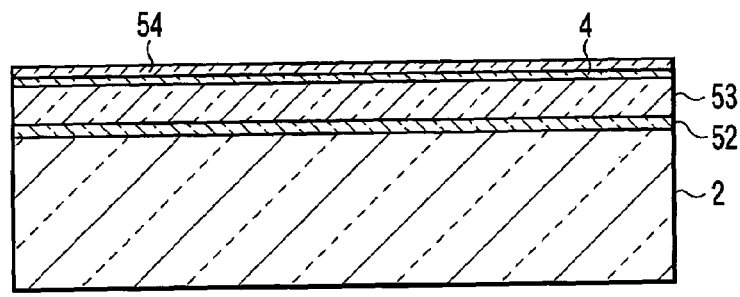
Figure 15B:
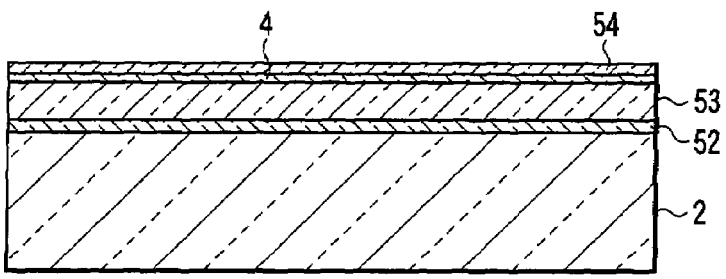

On the waveguide layer 4, as shown in FIGS. 14B and 15B, a layer 54 formed of a material whose refractive index is slightly lower than that of the waveguide layer 4, for example, single crystal Si is formed by sputtering or CVD. This structure is similar to that of an optical fiber, and the waveguide layer 4 corresponding to a core is surrounded with layers 53, 54 corresponding to a clad layer whose refractive index is lower than that of the waveguide layer 4. Therefore, a light wave is effectively guided through the waveguide layer 4.

Figure 14C:
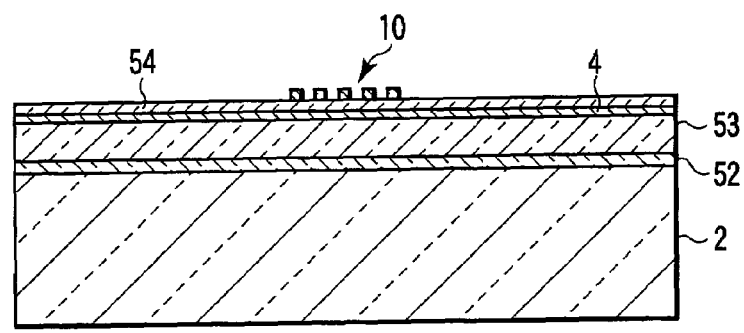
Figure 15C:
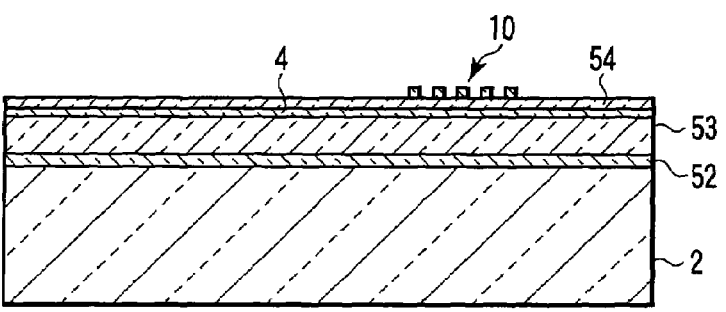

As shown in FIGS. 14C and 15C, a grating portion of an FGC 10 is formed in a region on the waveguide layer 4. A plurality of layers for diffraction grating are formed in the region on the waveguide layer 4 using a material similar to that of a layer 54, for example, single crystal Si, and using a mask. Thereafter, the photo resist is applied to the region on the grating layer, a diffraction grating pattern is transferred and exposed, and the photo resist is formed into a mask for the grating. The grating layer is selectively etched using the mask for the grating to form the diffraction grating, and the photo resist is removed.

Figure 14D:
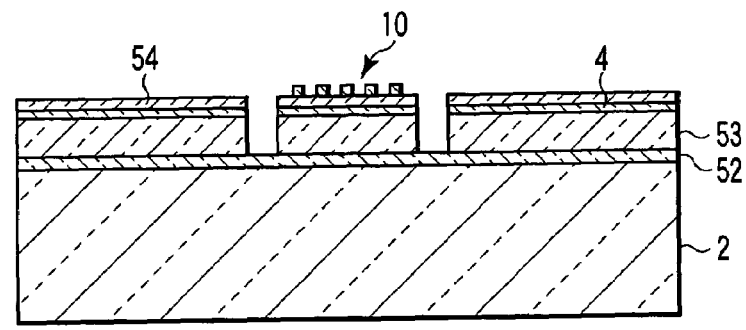
Figure 15D:
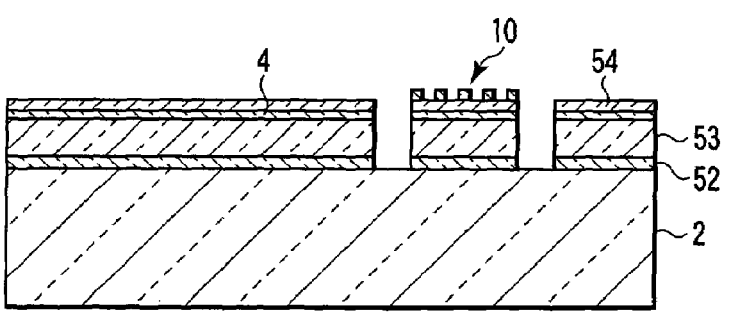

Thereafter, as shown in FIGS. 14D and 15D, the region on the waveguide layer 4 is formed into the FGC 10 which is a diaphragm. A conventional photolithography technique is similarly applied in forming the FGC 10. That is, the photo resist is applied onto the layer 54 having a substrate structure shown in FIGS. 14C and 15C, a diaphragm pattern is transferred/exposed, and a mask having patterns of the diaphragm and waveguide portion is prepared. The waveguide layer 4 is selectively etched using this mask to form the diaphragm and a waveguide portion 12 for supporting the plate. Thereafter, the photo resist is removed, and a substrate structure is prepared in which the FGC 10 and the waveguide portion 12 are independently formed on the substrate 2. Here, the waveguide portion 12 which is a spring for supporting the diaphragm is formed as a part of the waveguide of the waveguide layer 4 formed on the substrate 2.

Figure 14E:
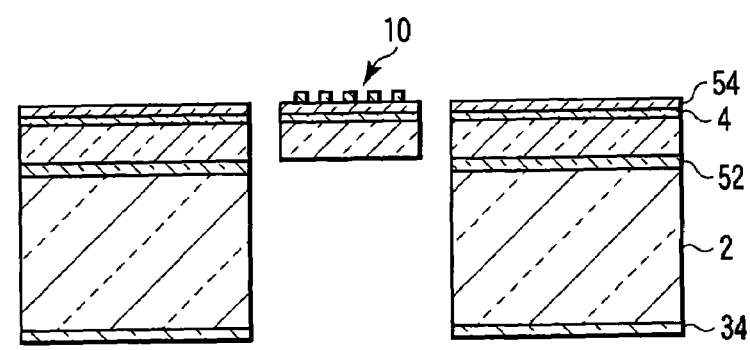
Figure 15E:
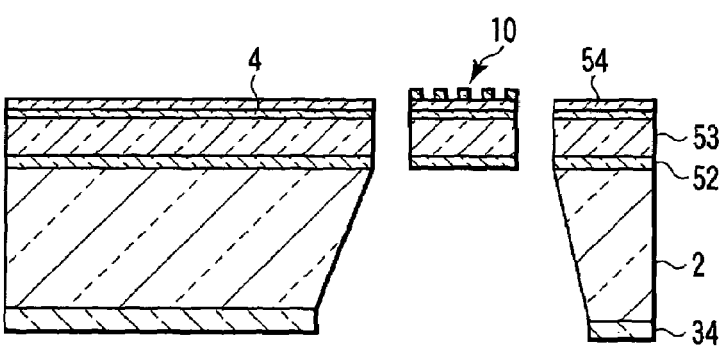

Finally, as shown in FIGS. 14E and 15E, the diaphragm on which the FGC 10 is formed using wet etching or the like is separated from the substrate 2. As shown in FIGS. 14E and 15E, a mask 34 is formed on the back surface of the substrate 2, and a hollow portion 8 is formed in the back surface of the FGC 10 by anisotropic etching. Here, it has been described that this hollowing process is anisotropically performed by the wet etching. The present invention is not especially limited to this example. The process may be isotropically performed by a dry process. As to a device in which the optical waveguide 4 is prepared by the above-described steps, an LD chip 14 is coupled with the optical waveguide 4 to complete an optical integrated microphone.

According to the above-described steps, the device can be similarly formed in the SOI substrate structure 60, and the steps are therefore useful for a structure which requires integration of a high-pressure resistant device.

Figure 16:
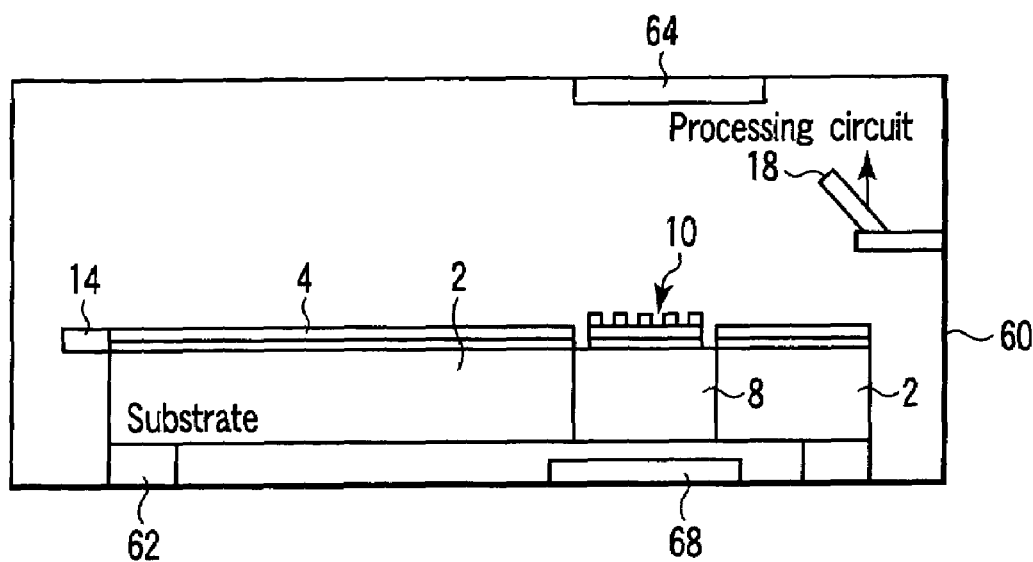
FIG. 16 is a sectional view schematically showing a microphone device in which the optical integrated microphone shown in FIG. 1 is received in a casing.

The optical integrated microphone shown in FIG. 1 is concretely mounted in a package (casing) 60 shown in FIG. 16. That is, the optical integrated microphone shown in FIG. 1 is disposed and fixed in the package 60 via an electric isolator 62. The photo detector 18 for detecting a light wave from the FGC 10 is fixed to a support plate 66 disposed in the package 60. Through holes 64, 68 which permit passage of a sound wave are disposed facing the FGC 10 and the hollow portion 8 in the package 60. By this mounting structure, a small-sized optical integrated microphone device can be constituted.

Figure 17:
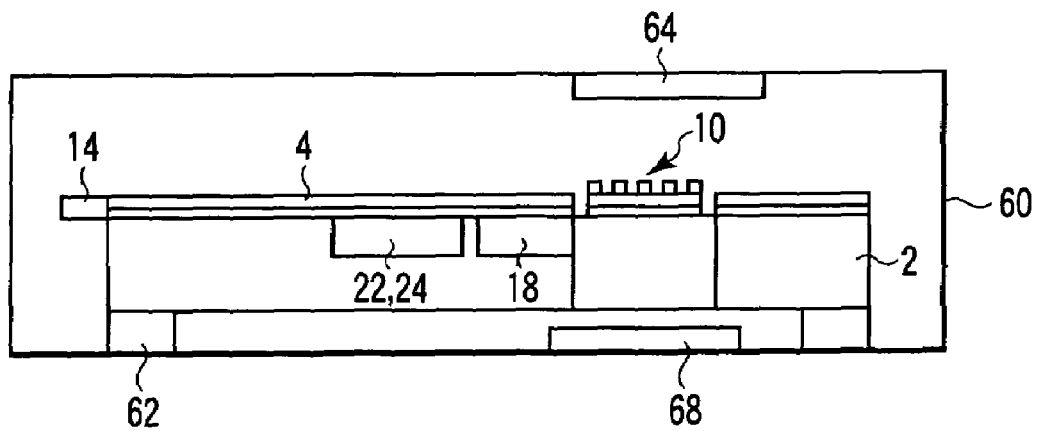
FIG. 17 is a sectional view schematically showing a microphone device in which the optical integrated microphone shown in FIG. 4 is received in a casing.
Figure 18:
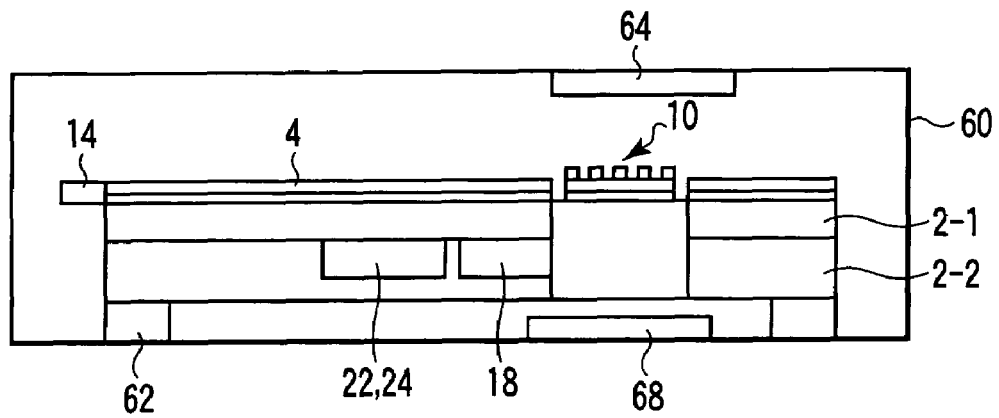
FIG. 18 is a sectional view schematically showing a microphone device in which the optical integrated microphone shown in FIG. 5 is received in a casing.
Figure 19:
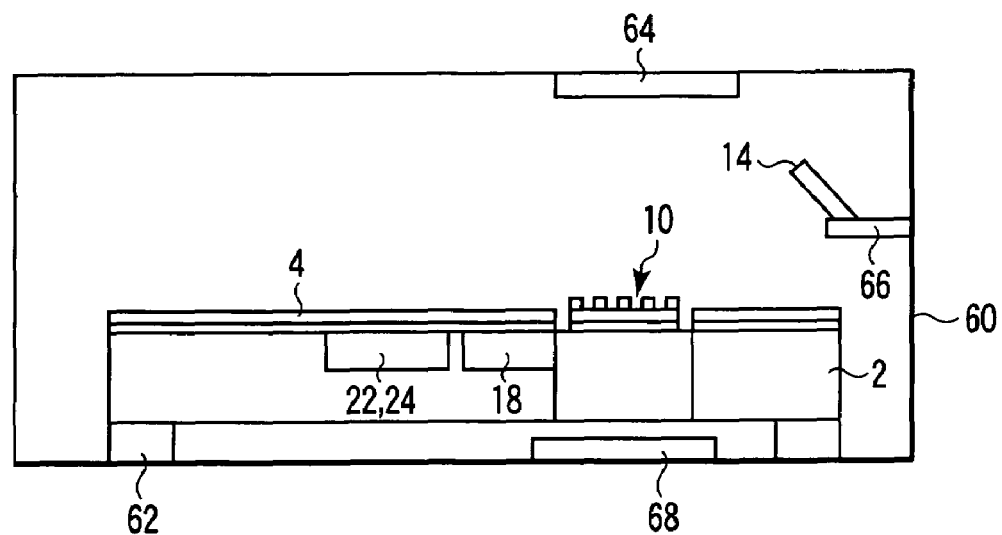
FIG. 19 is a sectional view schematically showing a microphone device in which the optical integrated microphone shown in FIG. 6 is received in a casing.

Similarly, the optical integrated microphones shown in FIGS. 4, 5, and 6 can be similarly mounted in packages (casings) 60 shown in FIGS. 17, 18, and 19, respectively, to constitute small-sized optical integrated microphone devices. The devices shown in FIGS. 17, 18, and 19 are denoted with the same reference numerals as those of the components of the device shown in FIG. 16, and the description is omitted. By this microphone device, a space in a two-dimensional or three-dimensional space direction can be reduced, and a system can be miniaturized.

In the acoustoelectric converter element described above, the optical waveguide which guides the light wave emitted from a light source into the diaphragm is formed on a semiconductor substrate, and the diffraction grating which focuses the light wave on a point of a free space is formed on the diaphragm. The diaphragm is connected to the substrate via a connection portion which guides the light wave. That is, the connection portion also acts as a spring via which the diaphragm hangs from the substrate. According to this structure, a light source which has heretofore been positioned in a three-dimensional space can be disposed in the same flat face as that of the substrate, and space saving can be achieved. Furthermore, a photo detecting device is formed on the semiconductor substrate, or a semiconductor chip on which the photo detecting device is formed is laminated onto the semiconductor substrate. Accordingly, it is possible to construct a hybrid type optical integrated system, and it is possible to provide a remarkably small-sized microphone which does not require any space in a three-dimensional direction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An acoustoelectric converter element for converting an acoustic wave to an electric signal utilizing a light wave, comprising:
   a frame member having a hollow space, the frame member being formed from a semiconductor substrate having a surface region, the surface region of the semiconductor substrate being removed to form the hollow space in the frame member;
   a first optical waveguide formed on the frame member, which is formed from an optical waveguide layer formed on the semiconductor substrate, the optical waveguide layer being etched as to form the first optical waveguide;
   a second optical waveguide arranged in the hollow space, the second optical waveguide being formed from the optical waveguide layer, the optical waveguide layer being etched as to form the second optical waveguide;
   a diffraction grating formed on the second optical waveguide;
   supporting members which couple the first optical waveguide to the second optical waveguide and support the diffraction grating and the second optical waveguide in the hollow space so as to vibrate with respect to the acoustic wave, the supporting members being formed from the optical waveguide layer, the optical waveguide layer being etched as to form the supporting members; and
   a light source which emits a light wave guided to the diffraction grating through the first optical waveguide, one of the supporting members and the second optical waveguide, the diffraction grating diffracting the light wave; and
   a photo-detector which detects the diffracted light wave.

2. The acoustoelectric converter element according to claim 1, wherein the light source includes a laser diode which is formed on the semiconductor substrate.

3. The acoustoelectric converter element according to claim 1, wherein the photo-detector is formed on the semiconductor substrate.

4. The acoustoelectric converter element according to claim 1, wherein the photo-detector is provided outside of the frame member.

5. An acoustoelectric converter element for converting an acoustic wave to an electric signal utilizing a light wave, comprising:
   a frame member having a hollow space, the frame member being formed from a semiconductor substrate having a surface region, the surface region of the semiconductor substrate being removed to form the hollow space in the frame member;
   a first optical waveguide formed on the frame member, which is formed from an optical waveguide layer formed on the semiconductor substrate, the optical waveguide layer being etched as to form the first optical waveguide;
   a second optical waveguide arranged in the hollow space, the second optical waveguide being formed from the optical waveguide layer, the optical waveguide layer being etched as to form the second optical waveguide;
   a diffraction grating formed on the second optical waveguide;
   supporting members which couple the first optical waveguide to the second optical waveguide and support the diffraction grating and the second optical waveguide in the hollow space so as to vibrate with respect to the acoustic wave, the supporting members being formed from the optical waveguide layer, the optical waveguide layer being etched as to form the supporting members; and
   a light source which emits a light wave guided to the diffraction grating, the diffraction grating diffracting the light wave; and
   a photo-detector which detects the diffracted light wave which is guided from the diffraction grating through the first optical waveguide, one of the supporting members and the second optical waveguide.

6. The acoustoelectric converter element according to claim 5, wherein the light source includes a laser diode which is formed on the semiconductor substrate.

7. The acoustoelectric converter element according to claim 5, wherein the photo-detector is formed on the semiconductor substrate.

* * * * *